United States Patent [19]

Yoshizato et al.

[11] Patent Number: 5,263,983
[45] Date of Patent: Nov. 23, 1993

[54] MEDICAL MATERIAL AND PROSTHETIC SKIN IN WHICH CELLS CAN INVADE

[75] Inventors: Katsutoshi Yoshizato, Ebina; Jun Konishi, Fuji; Mikio Koide, Fuji; Kaori Oyamada, Fuji; Ken-ichi Ohsaki, Fuji; Takeo Katakura, Fuji; Yuichi Mori, Tokyo; Ken Tatebe, Fuji, all of Japan

[73] Assignee: Terumo Kabushiki Kaisha, Tokyo, Japan

[21] Appl. No.: 576,493
[22] PCT Filed: Mar. 9, 1989
[86] PCT No.: PCT/JP89/00257
    § 371 Date: Sep. 7, 1990
    § 102(e) Date: Sep. 7, 1990
[87] PCT Pub. No.: WO89/08465
    PCT Pub. Date: Sep. 21, 1989

[30] Foreign Application Priority Data

| Mar. 9, 1988 | [JP] | Japan | 63-53837 |
| Jul. 25, 1988 | [JP] | Japan | 63-183478 |
| Jul. 25, 1988 | [JP] | Japan | 63-183479 |
| Sep. 6, 1988 | [JP] | Japan | 63-221337 |

[51] Int. Cl.⁵ .................................................. A61F 2/04
[52] U.S. Cl. ........................... 623/12; 128/DIG. 8; 424/428; 514/801
[58] Field of Search ............. 128/DIG. 8; 623/12; 514/801, 802, 822; 424/428, 94.64

[56] References Cited

U.S. PATENT DOCUMENTS

| 3,322,632 | 5/1967 | Schwick | 424/94.64 |
| 3,767,437 | 10/1973 | Cruz, Jr. | |
| 4,164,559 | 8/1979 | Miyata et al. | 424/428 |
| 4,276,281 | 6/1981 | Crihelair | 424/94.64 |
| 4,280,954 | 7/1981 | Yannas et al. | 606/229 |
| 4,522,753 | 6/1985 | Yannas et al. | |
| 4,642,117 | 2/1987 | Nyugen et al. | |
| 4,703,108 | 10/1987 | Silver et al. | 128/DIG. 8 |
| 4,749,689 | 6/1988 | Miyata et al. | 128/DIG. 8 |
| 4,970,298 | 11/1990 | Silver et al. | 128/DIG. 8 |

FOREIGN PATENT DOCUMENTS

0052288 11/1980 European Pat. Off.

Primary Examiner—David Isabella
Assistant Examiner—Gina M. Gualtieri
Attorney, Agent, or Firm—Burns, Doane, Swecker & Mathis

[57] ABSTRACT

Disclosed is a cell-penetrable medical material in which cells can invade, comprising denatured collagen with helix content of 0 to 80%, and carrier substance having higher resistance to enzyme decomposition than the denatured collagen. An artificial skin in which this medical material is used as the wound contact layer, and its preferred manufacturing methods are also disclosed.

13 Claims, 1 Drawing Sheet

F I G. 1

F I G. 2

MEDICAL MATERIAL AND PROSTHETIC SKIN IN WHICH CELLS CAN INVADE

TECHNICAL FIELD

The present invention relates to cell-penetrable medical material easily assimilable into living tissues and useful as artificial tissues. Further, the present invention also relates to application of this medical material to artificial skin.

BACKGROUND ART

Implantation is very effective for treating deficiency occurred in part of tissues or irreversible function deficiency. For avoiding the problem of immune incompatibility known as rejection, in this case, it is preferable to transplant the tissue coming from other regions of the patient or his relatives, namely allotransplantation. However, such favorable implanting tissues are not always available. So, such studies for providing implantable artificial tissues have heretofore been made.

First approach for getting artificial tissues free of rejection is to provide the material having low histological reactivity, namely the material which fails to sensitize the tissue and immunocellular system. An example of this approach is the study to enhance hydrophobicity of the synthetic polymer material represented by polyurethanes.

Second approach is to provide the material which is capable of assimilating rapidly into the tissue before inducing the immunoreaction thereby functioning as a part of an organ. More particularly, it is to construct the tissue similar to connective tissues by penetrating such a cell having the tissue-healing function as fibroblast into the material coming from living bodies such as collagen. Since the new tissue thus formed is no longer not-self, no immune incompatibility would take place. Therefore, it can be said that this approach is more ideal than the first approach.

However, said second approach has the following defects.

Artificial materials consisting of collagen or the like derived from living bodies show high affinity to cellular tissues, but would be easily decomposed by collagenase or other enzymes within the living bodies. Therefore, there cannot be sufficiently kept the time for the penetration of fibroblast or the like to construct new tissues. So it is necessary to enforce the physical properties of the material by introducing cross-linking with any means, in order that the material may resist against the decomposition due to collagenase. Dehydrating cross-linking under heating or chemical cross-linking with chemicals can be adopted therefore. Of these cross-linking methods, the dehydrating cross-linking is safer than the chemical treatment, but less resistant against collagenase than the chemical cross-linking. Therefore, it is general that the chemical cross-linking is adopted singly, otherwise a combination of the chemical cross-linking and the dehydrating cross-linking is adopted.

Resistance against collagenase is markedly improved by introducing the cross-linking structure by said methods. For example, when the cross-linking structure is introduced into a collagen by merely dehydrating the collagen under heating at 110° C. in vacuum for 24 hours, the cross-linked collagen is dissolved within one day by allowing to stand at 37° C. in 3 unit/ml collagenase solution. On the contrary, the collagen obtained by introducing the cross-linking structure with an isocyanate type cross-linking agent does not show any change on appearance in 7 days even by allowing to stand still at 37° C. in 1000 unit/ml collagenase solution.

On the other hand, introduction of said strong cross-linking structure would lower markedly the good affinity to cells or tissues, which is an inherent property of the collagen. Therefore, the penetration of cells would be inhibited to accompany a problem that the new desired tissues could not be formed.

As stated above, it is difficult to suffice both the requirement of good resistance to enzymes and the requirement of good affinity to cells or tissues in materials derived from living bodies such as collagen. Therefore, while the second approach is very attractive, no medical material sufficing the requirements has been developed yet.

The cell-penetrable medical material may be considered to be very useful as coating material for imbedding artificial organs or artificial vessels. However, its use as artificial skin is more realizable and effective.

Artificial skin is an artificial medical material used for coating temporarily or eternally the injured region in order to prevent bacterial infections or overflowing of the humor when any dermal tissue is injured by burning or ambustion. Thus, artificial skin a replacement of autograft skin.

As a wound coating material which can be used for the same purpose as in artificial skin, gauze, absorbent cotton and the like are heretofor used. However, these materials have a disadvantage that they have low inhibitory ability against bacterial infections. In addition, because they absorb rapidly the exudate, the surface of wound would be dried so much and accompanied by pain, bleeding or the like in peeling them. Although sometimes an ointment or the like is used together for avoiding said problem, in this case there would take place another disadvantage that the exudate is so insufficiently absorbed that the surface of wound become excessively moist.

When the surface of wound extends in a broad scope, the following coating films are used. First category includes silicone gauze, silicone rubber film, synthetic fiber sheet such as nylon, teflon or the like having velour-like superficial structure, and other synthetic materials. Second category includes lyophilizated pig's skin, chitin unwoven cloth, collagen film, polyamino acid sponge, mucopolysaccharide complex collagen film, and other materials derived from living bodies.

However, coating films made from said synthetic materials have disadvantages such as poor tight adhesion to the injured region and low steam permeability together with easy inclination to induce cracking. Further, said coating films derived from living bodies show comparatively better adaptability to living bodies but have difficulty in availability of raw material. Moreover, most of them have antigenicity as well as defects such as inclination to deteriorate by bacterial infection or contact with the exudate.

In addition to said coating films, certain complex film made from collagen-treated nylon mesh and silicone film has recently been developed and is commercially available. This complex film has favorable close adhesion to the surface of wound and appropriate water permeability. However, the complex film adheres to the surface of wound, because the granulation tissue enters into the nylon mesh in the course of curing. Since the nylon mesh remains in the granulation tissue without decomposition, after curing the complex film must be peeled together with remarkable pain.

DISCLOSURE OF THE INVENTION

A first object of the present invention is to provide cell-penetrable medical material which, because of having the desired resistance to decomposing enzymes, can keep the necessary mechanical strength over a certain period under in vivo circumstances together with favorable affinity to cells and tissues, and also to provide a process for preparing said material.

A second object of the present invention is to provide artificial skin which has a satisfactory function as a replacement of autograft skin, using said medical material, and also to provide a process for preparing it. Thus, artificial skin of the present invention can inhibit bacterial infection and overflowing of the body fluid by coating temporarily or eternally the surface of wound and ca accelerate sufficiently repairing the tissue due to cell growth.

The cell-penetrable medical material of the present invention comprises denatured collagen with helix content of 0 to 80%, and carrier substance having higher resistance against enzyme decomposition than the denatured collagen.

The first artificial skin of the present invention comprises a support layer composed of fibroin, a wound contact layer laminated on one side of the support layer, and moisture permeation regulating layer for controlling moisture permeation which is laminated on the other side of the support layer, wherein the wound contact layer contains denatured collagen with helix content of 0 to 80% and fibrous collagen. The fibrous collagen has a higher resistance against enzyme decomposition than the denatured collagen. That is, the fibrous collagen functions as the carrier substance of the denatured collagen. It is preferable to incorporate antibacterial agent into at least one layer of wound contact layer, support layer and moisture permeation regulating layer.

The second artificial skin of the present invention comprises a support layer composed of fibrous collagen matrix possessing crosslinking structure, a wound contact layer laminated on one side of the support layer, and a moisture permeation regulating layer for controlling the moisture penetration which is laminated on the other side of the support layer, wherein the wound contact layer contains denatured collagen with helix content of 0 to 80% and fibrous collagen. It is preferable to incorporate antibacterial agent into at least one layer of wound contact layer, support layer and moisture permeation regulating layer.

The method of manufacturing artificial skin of the present invention is for obtaining the foregoing first or second artificial skin. This method comprises the steps of:

a step of preparing a mixture solution containing denatured collagen with helix content of 0 to 80%, and fibrous collagen, a step of placing a fibroin membrane or a fibrous collagen membrane having crosslinking structure on the liquid surface of the mixture solution, and then performing lyophilization, thereby forming a laminate of a support layer composed of the fibroin membrane or the fibrillated collagen membrane, and a wound contact layer made of porous substance containing the denatured collagen and the fibrous collagen, a step of forming a viscous thin film made of a substance for providing a moisture permeation membrane, on a substrate having a peeling surface, a step of placing the surface of the support layer on the viscous thin membrane, and a step of drying the viscous thin film until hardened, and then heating for 1 to 24 hours at 50° to 180° C. in a vacuum of less than 0.05 Torr.

It is preferable to incorporate an antibacterial agent into at least one of the solution containing denatured collagen and fibrous collagen, the fibroin membrane or the fibrous collagen membrane having crosslinking structure, and the viscous thin film for providing the moisture permeation regulating layer.

The invention is described in further detail below.

CELL-PENETRABLE MEDICAL MATERIAL

The cell-penetrable medical material of the present invention is realized on the basis of the discovery that cells can easily invade into a collagen layer in which collagen has been denatured up to the helix content of 0 to 80%.

To begin with, the denatured collagen with helix content of 0 to 80% is explained below. The helix content refers to the content of the triple chain helix which is characteristic of collagen. In the denatured collagen, any part or all of the triple chain helix is transformed into random coil. Therefore, [1-helix content] corresponds to the degree of denaturing. The denatured collagen is obtained by heating, chemical treatment, or physical treatment of collagen. The most preferable method for obtaining the denatured collagen is heat treatment.

Such denatured collagen is prepared, for example, in the following manner. The collagen material derived from the bovine corium is treated in acid or alkali, and collagen composed of triple chain helix is obtained. Successively, in the presence of water, the collagen thus obtained is heated for 20 minutes to 24 hour at 50 to 125° C., preferably 90° to 121° C., thereby denaturing the triple chain helix into random coil. For example, when heated for 30 minutes at 60° C., the helix content becomes about 40%. Or when heated for 24 hours at 100° C., the helix content will be 0%. The helix content can be measured by the circular dichromism spectrometer (CD) or infrared spectrophotometer (P. L. Gorden et al., Macromoles, 1(6), 954, 1974; M. Nakura, Hashimoto, et al., High Polymer Article Collection, 41(8), 473, 1984). The values of helix content cited in this specification are the results calculated on the basis of spectroscopic measurements. Incidentally, from the results of test on electrophoresis, it has been found that part of collagen molecule was cleaved in this denatured collagen.

The denatured collagen used in this invention has the helix content of 0 to 80% as mentioned above, or preferably 0 to 50%. It is also desired to use the denatured collagen in which the antigenic portion (teropeptide) at the terminal of the collagen molecule has been removed. Such collagen lack of antigenicity and free of this teropeptide is generally known by the tradename of Aterocollagen. Aterocollagen is obtained by treating the starting collagen with acid or alkali, and then treating with pepsin which specifically acts on the teropeptide.

Since the helix of the denatured collagen used in the medical material of the invention is transformed into random coil and partly cleaved on the way, it seems that cells can invade easily into the denatured collagen. On the contrary, this denatured collagen is likely to be decomposed relatively rapidly by collagenase, and cannot maintain itself sufficiently until new tissues are built up by penetration of fibroblasts. Therefore, it is necessary that the medical material of the present invention contains not only the denatured collagen but also the carrier substrate having high resistance against enzymatic decomposition by collagenase or the like, in order to maintain a necessary mechanical strength for a certain period in the environments of the living body. This carrier substance is explained below.

The carrier substance used for this purpose is required to be capable of resisting against the action of decomposing enzyme until the invasion of cells is sufficiently promoted, and be also biocompatible. Examples of such substance may include polyester, polyurethane, vinyl chloride and other synthetic resins. However, more preferable carrier substances are biological substances such as collagen, fibroin, polylactic acid, mucopolysaccharides, and arginic acid, which are finally absorbed in the living body. What is particularly preferable is collagen, and more specifically preferred is Aterocollagen lacking of the teropeptide which has antigenicity.

The collagen used as the carrier substance is, naturally, undenatured collagen which has not been subjected to the denaturing treatment described above. More preferably, it should be a collagen in which crosslinking structure is introduced. The method of introducing crosslinking structure into collagen may comply with the conventional process, for example, the collagen may be heated or treated with crosslinking agent. In the case of heat treatment, the collagen is heated at 50° to 180° C. for 1 to 24 hours, preferably at 10° to 120° C. for 2 to 8 hours in a vacuum of less than 0.05 Torr, thereby performing thermal dehydration. When treating with crosslinking agent, the crosslinking agent to be used is not particularly limited. For example, aldehyde crosslinking agents such as glutaraldehyde, isocyanate crosslinking agents such as hexamethylene diisocyanate, and carbodiimide crosslinking agents such as 1-ethyl-3-(3-dimethylaminopropyl)carbodiimide hydrochloride may be used.

The fibrous collagen may be also used preferably as such carrier substance. The fibrous collagen is prepared by neutralizing the collagen composed of triple chain helix, by using phosphate buffer at 37° C. Thus, the water-soluble and dispersant triple chain helix structure is reconstructed into fibrous structure having periodicity, and the collagen is made insoluble.

The crosslinked fibrous collagen obtained by introducing a crosslinking structure into the fibrous collagen is particularly preferable carrier substance. The dispersant triple chain collagen is not particularly enhanced in the properties such as mechanical strength by introducing crosslinking structure, but when crosslinking structure is introduced into fibrillated collagen, the properties such as mechanical strength are remarkably improved owing to the synergic effects of the fibrous structure and the crosslinking structure. The crosslinking structure is introduced after forming the fibrous structure. When the degree of crosslinking introduced into the fibrous collagen is too low, sufficient physical strength will not be obtained. On the contrary, when it is too high, the structure and preferable properties of the collagen are sacrificed. Therefore, it is necessary to set appropriately the crosslinking-degree depending on the conditions. When using a crosslinking agent, an appropriate degree will be obtained at the concentration of crosslinking agent of, generally, 0.01 to 5% (w/v), or preferably 1 to 3% (w/v).

With the medical material of the present invention has an excellent cell-penetrating property due to the denatured collagen mentioned above, a sufficient strength may be maintained until corium-like connective tissues are formed by sufficient cell-penetration because of the combined use of carrier substance. In other words, the carrier substance in the denatured collagen forms a skeletal structure resisting against the decomposition action of enzyme. In addition, when biological substance such as collagen are used as the carrier substance, the carrier substance will be finally decomposed by the enzyme action. Therefore, it is completely assimilated in the body. Meanwhile, the ratio of denatured collagen to the carrier substance may be about 5 to 80% (w/v), or preferably 10 to 50% (w/v).

The medical material of the present invention may be embodied in various forms depending on the applications, such as film and sponge. In the embodied form, the carrier substance may be merely dispersed in the denatured collagen. Or, for example, the denatured collagen may be impregnated in the spongy matrix of the carrier substance.

The method for manufacturing the medical material of the present invention is exemplified below. Although collagen is used as carrier substance in the following method, the same method may be also applied using other material than collagen as the carrier substance.

In a first method, first of all, a collagen aqueous solution is prepared, and it is divided into two halves. The first half portion is let stand as it is, and the second half is heated to denature the collagen. Thus obtained denatured collagen solution and undenatured collagen solution are mixed, and are made into a desired form. For example, the mixture may be formed into a film by solvent casting method, or into a porous sponge by freeze-drying method. Afterwards, as required, the film or sponge is subjected to thermal crosslinking or chemical crosslinking.

In a second method, using only the undenatured collagen solution obtained in the above method, a porous film or porous sponge is formed in the same manner as described above. The film or spongy matrix thus obtained is then subjected to thermal crosslinking or chemical crosslinking. Thereafter, the matrix is immersed in denatured collagen solution, and dried in air or in vacuum or freeze-dried.

The ratio of denatured collagen to carrier substance is about 5 to 80% (w/v), or preferably 10 to 50% (w/v).

ARTIFICIAL SKIN

Figure 1:
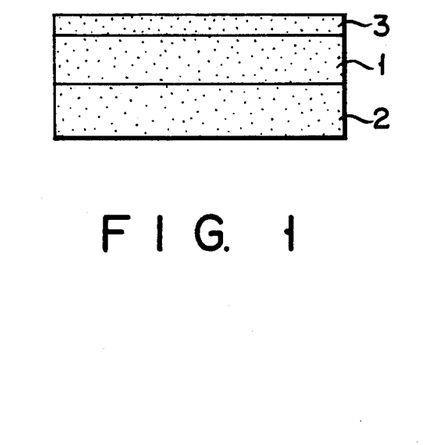
FIG. 1 is a sectional view showing an example of a multilayer structure in an artificial skin of the present invention.

The artificial skin of the invention is a multi-layer complex film using the aforementioned cell-penetrable medical material, and typically it is a complex film of three-layer structure as shown in FIG. 1. In FIG. 1, numeral 1 denotes a support layer. A wound contact layer 2 is laminated on the lower side of the support layer 1, and a moisture penetration regulating layer 3 is laminated on the upper side of the support layer 1. The cell-penetrable medical material is used in the wound contact layer 2. These layers are individually described below.

(1) Wound contact layer 2

As the wound contact layer 2, the foregoing cell-penetrable medical material using fibrous collagen as the carrier substance is particularly employed. That is, the wound contact layer 2 is composed of denatured collagen with the helix content of 0 to 80% and fibrous collagen. Composition and the like of the wound contact layer comprising these components are omitted herein, because they are already described above. Of course, the wound contact layer, like the medical material mentioned above, may be formed in desired forms such as film and sponge. The carrier substance may be merely dispersed in the denatured collagen. Or, for example, the denatured collagen may be impregnated in the spongy matrix of the carrier substance.

The functions of the wound contact layer 2 are to directly cover the wound surface to protect softly, suppress the pain, give moderate moisture, and prevent bacterial infection. It is also intended to promote new tissue formation by cell proliferation, and to encourage healing. The wound contact layer 2 made of such cell-penetrable medical material possesses all these functions, and it is particularly excellent in promotion of new tissue formation. More, specifically, when applied on the wound surface, macrophages, neutrophils and other inflammatory cells infiltrate, and fibroblasts invade in early phase. As a result, colium-like connective tissues are built up, and healing of the wound is encouraged. Concerning the invasion of cells, further explanation is omitted herein because it is already described in detail on the medical material. Finally, the wound contact layer 2 completely decomposed by enzymes and absorbed in the body. Therefore, unlike the conventional artificial skin, it does not accompany a striking pain upon removing after healing.

(2) Support layer 1

The support layer 1 is to reinforce the mechanical strength of the wound contact layer 2, and allow the cells to invade into the wound contact layer 2 smoothly.

As mentioned above, the wound contact layer possesses a specified resistance to collagenase by the combined use of fibrous collagen. However, the mechanical strength for covering material is still insufficient, and since it is finally assimilated in the body, it requires any support body for protecting it from external stimulation. Therefore, the support layer 1 is required to possess a specific mechanical strength. At the same time, the support layer 1 should not impede invasion of cells into the wound contact layer 2. As the material for satisfying these conditions, fibroin is used in the first artificial skin. In the second artificial skin, fibrous collagen with crosslinking structure is employed.

Fibroin is a biological material, and is a protein which is a nein constituent of silk. As known from the fact that silk thread is used as surgical suture, fibroin is a protein excellent in stability in living bodies. Aqueous solution of fibroin can be prepared by dissolving fibroin in a concentrated neutral solution of salts such as lithium bromide or calcium chloride and subjecting the solution to dialysis or the like. This aqueous solution of fibroin is freezed at $-18°$ C. to $0°$ C. and defrosted to form $\beta$-type crystalline structure, thereby giving water-insoluble porous unwoven cloth [Jun Umagoshi, Kobunshi Kagaku (Polymer Chemistry), 30, 582 (1973)]. This porous unwoven cloth of fibroin shows more excellent stability in living bodies than ordinary collagen having crosslinking structure. So, it is appropriately used as a supporting layer of artificial skin used for coating the surface of would over a long period of time.

The fibrous collagen with crosslinking structure is as mentioned above. That is, when crosslinking structure is introduced to fibrous collagen, the mechanical strength and other properties are markedly enhanced by the synergistic action of fibrous structure and crosslinking structure. Therefore, it is favorably used as the support layer of artificial skin.

(3) Moisture Permeation Regulating Layer 3

Moisture permeation regulating layer 3 functions to control water content on the surface of wound during artificial skin is applied on the surface of wound. Pooling exudate on the surface of wound can be avoided while keeping the surface of wound wet and moist, by ensuring appropriate steam permeation with this moisture permeation regulating layer 3. At the same time, transudation of the protein ingredients in the exudate outside can be prevented, thereby making favorable circumstances for repairing tissues. It is heretofore well known that such moisture permeation regulating layer is used in wound coating material, and these known materials can be also used for artificial skin of the present invention. Thus, a film of non-toxic material having about 0.1 to 1 $mg/cm^2$/hour of water flux can be used as such moisture permeation regulating layer 3. Its appropriate thickness is about 5 to 200 $\mu m$. Non-toxic materials include silicone resin, polyacrylate ester, polymethacrylate ester, polyurethane and the like. In particular, silicone resin is preferred.

Said artificial skin having three layers can exhibit very excellent therapeutic effect as artificial skin, because wound-contacting layer 2 has favorable cell-penetration and appropriate resistance against enzymic decomposition, satisfactory mechanical strength is given by supporting layer 1 and appropriate moisture content is kept on the surface of wound by moisture permeation regulating layer 3. Since an improvement of cell-penetration and resistance to enzymes, both of which were heretofore incompatible, have been attained in wound-contacting layer 2, there can be obtained by far more excellent therapy accelerating effect than known wound coating materials.

In preferred embodiments of said first and second artificial skin, antibacterial agent is incorporated in at least one of such wound-contacting layer 2, supporting layer 1 and moisture permeation regulating layer 3. Appropriate antibacterial agents include silver sulfadiazine, gentamycin and silver nitrate. However, various other antibacterial agents can be used without limiting to them. Incorporation of such anti-bacterial agents is a means for preventing effectively antibacterial infection.

Bacterial infection is apt to occur in broad ambustion or serious ambustion (for example, degree III ambustion). Cream base containing antibacterial agent has heretofore been used for preventing such bacterial infection. However, when cream base is used together with known wound coating material such as gauze or bandage, about 57% of the applied cream soaks into gauze or the like together with the exudate and about 21% of the cream only gets to the surface of wound. Further, the cream has to be applied everyday to need troublesome labour. On the contrary, if the artificial skin of the present invention contains antibacterial agent, it can release gradually the antibacterial agent in a certain period. Therefore, the antibacterial agent can act continuously without exposing the surface of wound to ambient air and without troublesome labour in applying the antibacterial agent to the wound everyday, whereby bacterial infection can be prevented effectively in combination with bacterial penetration-preventive effect of the moisture permeation generating layer.

Figure 2:
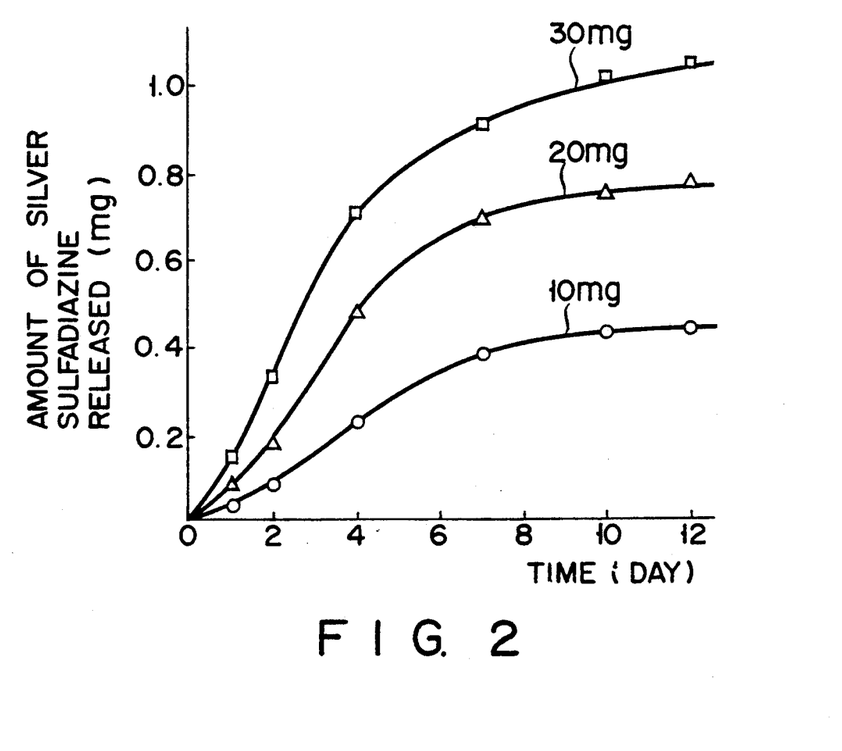
FIG. 2 is a graph showing the results of investigation of the release rate of the antibacterial agent contained in the moisture penetration regulating layer in the artificial skin in FIG. 1.

The following experiment was performed for examining the aspect of releasing antibacterial agent contained in moisture permeation regulating layer 3. At first, three silicone films (about 0.15 g) of 20 μm thick in size (5 cm×5 cm) were prepared, which respectively contain 10 mg, 20 mg and 30 mg of silver sulfadiazine (AgSD). These respective samples were dipped in 100 ml of distilled water, and the amount of AgSD eluted was measured in the lapse of time, respectively. The result is shown in FIG. 2. In this Figure, the abscissa shows the lapse of time (day) and the ordinate shows the cumulative amount of AgSD eluted. It is observed from the result that AgSD contained in the silicone film is gradually released to attain the gradual releasability enough to get the effect described above.

When a main object is to prevent bacterial invasion from outside and it is necessary to add antibacterial agent into any one of these layers, it is preferred to select moisture permeation regulating layer 3. On the other hand, when the surface of wound is already infected by bacteria and a lot of antibacterial agent is needed to be applied on the wound, it is desirable to incorporate antibacterial agent into either wound-contacting layer 2 or supporting layer 1. Of course, one can incorporate antibacterial agent into any two or three members of wound-contacting layer 2, supporting layer 1 and moisture permeation regulating layer 3.

MANUFACTURING METHOD OF ARTIFICIAL SKIN

The manufacturing method of artificial skin of the invention is a process for efficiently preparing either first or second artificial skin, having a wound contact layer in which the carrier substance is merely dispersed in the denatured collagen. This method may be easily realized by the following steps a) to f).

a) In the first place, a collagen aqueous solution is prepared, and is divided into two halves. One half portion is let stand as it is, while the other half portion is heated to denature the collagen. Thus obtained denatured collagen solution and undenatured collagen solution aremised. The obtained mixed solution is used for forming the wound contact layer 2.

b) Separately, fibroin film or fibrous collagen film with crosslinking structure, which is used as the support layer 1, is formed.

The fibrous collagen film with crosslinking structure is formed into a porous spongy film by freeze-drying the aqueous solution of crosslinked fibrous collagen prepared by the previously mentioned method.

The fibroin film is also manufactured into porous film by the method already described.

c) In the next step, the mixed solution is received in a certain container, and the fibroin film or the fibrous collagen film with crosslinking structure is put on the liquid surface, and is freeze-dried. As a result, a laminate of the support layer 1 and wound contact layer 2 is obtained. In this case, the support layer 1 is a fibroin film or a fibrous collagen film with crosslinking structure, and the wound contact layer 2 is a porous layer containing denatured collagen and fibrous collagen.

d) On a substrate having a peeling surface such as Teflon substrate, a solution of a substance such as silicone for affording moisture permeable film is developed, and a viscous thin film is formed.

e) On the viscous thin film, the laminate of support layer 1 and wound contact layer 2 is placed in such manner that the support layer 1 contacts with the viscous thin film.

f) After the viscous thin film is dried until hardened, in a vacuum of less than 0.05 Torr, it is further heated for 1 to 24 hours at 50° to 180° C. As a result, the viscous thin film is dried, and the moisture permeation regulating layer 3 is formed. At the same time, the regulating layer 3 is integrally bonded on the support layer 1. Thus is obtained the artificial skin in three-layered structure as shown in FIG. 1.

In this way, according to the method of the invention, without using any adhesives, an artificial skin in laminate structure as shown in FIG. 1 may be easily manufactured.

Meanwhile, a preferred artificial skin containing antibacterial agent may be manufactured by incorporating an antibacterial agent at least into one of the mixed solution for forming the wound contact layer 2, the fibroin film or the fibrous collagen film with cross-linking structure to be used as support layer 1, or the solution containing the substance for offering the moisture permeation regulating layer 3.

DESCRIPTION OF THE PREFERRED EMBODIMENTS

The invention is now described in further details by way of examples.

<A> EXAMPLES OF CELL-PENETRABLE MEDICAL MATERIAL (EXAMPLES 1 to 4)

Example 1: Preparation of Aterocollagen/denatured Aterocollagen Matrix 1.0 g of aterocollagen (AC) was dissolved in diluted hydrochloric acid at pH3.0.

This solution was kept in a 60° C. thermostatic oven for 30 minutes, and was left stand at room temperature for 2 hours to obtain a solution of denatured aterocollagen (HAC). The helix content of thus obtained HAC was about 40%. While stirring 0.3 w/v % AC (pH3.0) solution, 0.3 w/v % HAC solution was added to the AC solution and mixed. This solution was poured into a stainless steel vat, and was directly frozen quickly to −30° C., and after sufficient freezing, it was freeze-dried in a vacuum of less than −40° C./0.1 Torr. The product was thermally dehydrated and crosslinked by heat treating for 24 hours at 110° C. in a vacuum of less than −40° C./0.1 Torr.

Reference 1: Preparation of AC Matrix 1.0 g of AC was dissolved in diluted hydrochloric acid at pH3.0 up to the concentration of 0.3 w/v %. This solution was freeze-dried in the same manner as described above, and was further heated, dehydrated and crosslinked.

Test 1: In Vitro Cell Invasion Test of AC/HAC Matrix

Cell invasion into matrices obtained in Example 1 and Reference 1 was evaluated by conducting in vitro culture test using rat skin fibroblasts.

A collagen sponge of 3.5 cm in diameter was put on a 60 mm sterilized Petri dish (manufactured by Termo), and fibroblasts were dropped on the sponge by 1 ml at a concentration of $1 \times 10^6$ cells/ml, and cultivated for 24 hours at 37° C. Furthermore, 3 ml of DME culture medium containing 10% FBS was added and cultivated for 6 days at 37° C.

After fixing in 10% neutral buffer malin solution, the specimen was stained and observed by optical microscope. The results of evaluation are shown in Table 1.

TABLE 1

| | In vitro cell invasion test into collagen matrix | |
|---|---|---|
| Specimen | Cell invasion | Sponge from retaining ability |
| AC | − | +++ |
| AC - 20 wt. % HAC | ± | +++ |
| AC - 33 wt. % HAC | +++ | +++ |
| AC - 50 wt. % HAC | +++ | +++ |
| AC - 67 wt. % HAC | +++ | +++ |
| AC - 80 wt. % HAC | +++ | + |

Note:
| | Cell invasion | Sponge form retaining ability |
|---|---|---|
| − | None | Eliminated (dissolved) |
| ± | Slight invasion | Almost dissolved |
| + | Small invasion | Extreme deformation although specimen remained |
| ++ | Medium invasion | Slight contraction, dissolving |
| +++ | Marked invasion | Unchanged |

It is known from Table 1 that the matrix mixed with HAC was notably improved in the cell invasion as compared with the matrix of AC alone. However, from the viewpoint of retaining the sponge shape, it seems desired to contain the HAC by less than 80 wt. %.

Reference 2: Preparation of Fibrous AC 1.0 g of AC was dissolved in diluted hydrochloric acid at pH3.0 to obtain 0.3 w/v % solution. While stirring this solution in 4° C. thermostatic oven, phosphate buffer was added into the solution to prepare collagen solution with the final concentration of 0.1% (w/v) aterocollagen, 30 mM disodium phosphate, 100 mM NaCl. The collagen solution was immersed in 37° C. thermostatic bath for a day, thereby obtaining fibrous collagen (FC) solution. This solution was centrifuged (5000 rpm, 10 minutes), and concentrated, and 0.3% (w/v) fibrous aterocollagen (FC) solution was prepared. This solution was quickly frozen at −30° C., and then freeze-dried to prepare sponge. This sponge was heated in a vacuum at 110° C. for 2 hours to be dehydrated and crosslinked.

Example 2: Preparation of Fibrous Aterocollagen/denatured Aterocollagen Matrix

Mixing the 0.3% (w/v) FC solution and the 1% (w/v) HAC solution prepared in Example 1 at 37° C., the mixture was stirred for an hour. This solution was quickly frozen at −30° C., and was freeze-dried to prepare sponge. Afterwards, the sponge was treated in a vacuum at 110° C. for 2 hours to be heated, dehydrated and crosslinked.

Test 2: In Vitro Cell Invasion Test of Fibrous Aterocollagen/denatured Aterocollagen Matrix Cell invasion into the matrices obtained in Example 2 and Reference 2 was evaluated, by conducting in vitro culture experiment using rat fibroblasts in the same operation as in Test 1. The results of evaluation are shown in Table 2.

TABLE 2

| | In vitro cell invasion test into collagen matrix | |
|---|---|---|
| Specimen | Cell invasion | Sponge from retaining ability |
| FC | + | +++ |
| FC - 10 wt. % HAC | ++ | +++ |
| FC - 20 wt. % HAC | +++ | +++ |
| FC - 50 wt. % HAC | +++ | +++ |

As shown in Table 2, the matrices comprising FC were all excellent in the sponge form retention, and superior in stability. As for invasion of cells, although a slight deviational cell invasion was noted in FC alone, many cells invaded uniformly and dispersantly in the HAC added series. Further, the sponge shape of HAC added series was close to the in vivo tissues, in spite of the in vitro culture experimental system.

Test 3: In Vivo Subcutaneous Embedding Test of Fibrous Aterocollagen/denatured Aterocollagen Matrix The matrices prepared in Example 2 and Reference 2 were embedded in the rat skin, and tissue images were researched pathologically.

For subcutaneous transplantation (embedding) female Wistar KY rats weighing about 200 g were used. Before embedding, the rats were anesthetized with Nembutal diluted five times, and the dorsal hair moistened with surgical Isodine (Meiji Seika) was carefully clipped completely by a clipping razor. The clipped dorsal surface was disinfected with Isodine and ethanol. From each cut, the incision is widened so as to form a free gap in the areola tissues beneath the dermal muscle of rat (the adjacent cuts should not communicate with each other). The specimen was inserted into the gap, and was laid down flatly. The wound is sutured by nylon thread with corner needle. The wound was stitched with three sutures. The same specimen was embedded similarly in other rat.

On the 3rd day and the 28th day after embedding, the animals were killed by using ether or Nembutal diluted twice. Dermal tissues on the dorsal muscle of rat was cut out in a size of 8 cm by 12 cm or larger, keeping the embedded specimen in tissues. The tissue was put in 10% neutral buffer formalin solution, and let stand overnight to be fixed, and was presented for histopathological examination.

Histopathological search was started by cutting out the specimen from the tissues. In order that the specimen be securely contained, the tissues were cut in a strip of about 0.5 cm by 2.5 cm. It was penetrated through ethanol and then xylene, and was finally replaced by paraffin. After replacing, the tissues containing the specimen were put in a hot molten liquid of solid paraffin, and cooled quickly to finish paraffin embedding. The paraffin embedded tissues were sliced by means of rotary microtome of Yamato, and 4 μm thick paraffin segments were obtained. After removing paraffin, the specimen was stained histopathologically in an arbitrary staining method to complete the preparation. As the histopatological staining, hematoxylineosin (HE) staining, azane staining, resorsin-fuchsin staining, and other methods may be employed. The results are shown in Table 3.

TABLE 3

Histopatological changes in subcutaneous embedding test

| Specimen | Tissue changes | | |
|---|---|---|---|
| | Day 3 | | Day 28 |
| | Neutrophil infiltration | Fibroblast invasion | Granulation tissue atrophy |
| FC | +++ | ++ | +++ |
| FC - 10 wt. % HAC | + | +++ | + |
| FC - 20 wt. % HAC | ++ | +++ | + |
| FC - 50 wt. % HAC | +++ | ++ | + |

With FC alone, on the 3rd day, the neutrophil infiltration was intense, and fibroblast invasion was moderate, and on the 28th day, the formed granulation tissues were atrophied. By contrast, when HAC was contained by 10 or 20 wt. %, on the 3rd day, the neutrophil infiltration was weak, while the fibroblast invasion was more smooth. On the 28th day, the atrophy of granulation tissues was notably lessened.

Example 3: Preparation of Crosslinked Collagen Coated with Denatured Collagen

The freeze-dried sponge of fibrous aterocollagen (FC) obtained in Reference 2 was immersed overnight in 0.01% and 1% hexamethylene-di-isocyanate (HDI)-/ethanol solution, and chemical crosslinking was introduced. To each sponge, the aqueous solution of denatured collagen (HAC) obtained in Example 1 was added by 30 ml. After sufficient immersion, it was freeze-dried again to obtain sponge, which was heated for 2 hours in a vacuum at 110° C., and was further heated for 24 hours to be dehydrated and crosslinked. Thus, the collagen matrix coated with denatured collagen (HAC) was obtained. The final composition was adjusted so that the content of HAC be 10 wt. %.

Reference 3: Preparation of Crosslinked Collagen

The freeze-dried sponge of fibrous aterocollagen (FC) alone (crosslinked in the same procedure as in Example 3) was prepared as Reference 3, in the same manner as Example 3 except that the step of addition of aqueous solution of denatured collagen (HAC) was omitted.

Test 4: In Vivo Subcutaneous Embedding Test of Denatured Collagen Coated Crosslinked Collagen Matrix The matrices prepared in Example 3 and reference 3 were embedded beneath the rat skin in the same procedure as in Test 3, and histopathological examinations were conducted. However, the specimens were taken out on 7th day and 14th day. The results are shown in Table 4.

TABLE 4

Histopatological changes in subcutaneous embedding test

| Specimen | Crosslinking condition | Tissue changes on 7th day and 14th day | | |
|---|---|---|---|---|
| | | Neutrophil infiltration | Fibroblast invasion | Self-tissue making |
| FC | 0.01% HDI crosslinking + thermal crosslinking 2 hrs | ++ | − | − |
| HAC coated FC | 0.01% HDI crosslinking + thermal crosslinking 2 hrs | + | +++ | +++ |
| FC | 1% HDI crosslinking + thermal crosslinking 2 hrs | ± | − | − |
| HAC coated FC | 1% HDI crosslinking + thermal crosslinking 2 hrs | + | + | + |
| FC | 1% HDI crosslinking + thermal crosslinking 24 hrs | − | − | − |
| HAC coated FC | 1% HDI crosslinking + thermal crosslinking 24 hrs | ++ | ++ | ++ |

In each comparative example of FC, although there was partly invasion of neutrophils, the infiltration of the cell components themselves was very poor, including the inflammatory and reticuloendothelial cells. By contrast, in each HAC coated FC, the infiltration of cell components was very smooth, and partly self-tissue making was noted while foreign matter reaction was slightly strong in some cases. Particularly, in the specimen of HAC coated FC (0.01% HDI crosslinking+-thermal crosslinking 2 hours), a structure extremely similar to the corium in which even the neutrophil infiltration has been already reduced was rebuilt. Thus, it may be regarded as a nearly ideal matrix in view of the objects of the present invention.

Example 4: Preparation of Collagen Sponge Containing Silicone Film

On a teflon substrate, a hexane solution of 50% Silastic silicone adhesive type A (Dow Corning) was applied by using a precise applicator to form a film. Immediately after application, the sponge manufactured according to Example 3 was put on, and left stand at room temperature for about 10 minutes, and was hardened in an oven for at least an hour at 60° C.

Test 5: Transplantation Test in Skin Defect Wound

The sponge prepared in Example 4 was transplanted in a skin defect wound of rat. More specifically, in the dorsal skin of rat, a total skin defect wound (2 cm by 2 cm) with an exposed subcutaneous muscular membrane was prepared, and the specimen having a silicone film adhered on the superficial layer was ligated and sutured on the wound surface. The animals were killed in 4 weeks after transplantation, and the transplanted material and wound bed were cut out, and presented for pathological examinations. In 4 weeks, contraction of wound was not clearly observed, and a favorable granulation tissue was formed and regeneration of the cuticle was recognized.

\<B\> EXAMPLES OF PROSTHETIC SKIN AND ITS MANUFACTURING METHOD

Example 5

1) Preparation of wound contact layer

Preparation of fibrous collagen/denatured collagen matrix 1.0 g of AC was dissolved in diluted hydrochloric acid at pH3.0 to 0.3 w/v %. While stirring this solution in a 4° C. thermostatio oven, phosphate buffer was added to prepare collagen solution with the final concentration of 0.1 w/v % aterocollagen, 30 mM phosphate-2-sodium, 100 mM NaCl. Immersing overnight in a 37° C. thermostatic oven, fibrous collagen (FC) solution was obtained. This solution was centrifuged (5000 rpm, 10 minutes) and concentrated, and 0.3 w/v % fibrous aterocollagen (FC) solution was prepared. On the other than, 1.0% aterocollagen (pH3.0 hydrochloric acid) solution was treated for 30 minutes in a 60° C. therostatic oven, and was left stand at room temperature for 2 hours, and a solution of denatured aterocollagen (HAC) was obtained. Thus prepared solutions were mixed at 37° C., and stirred for an hour. This mixed solution was quickly frozen at −30° C., and freeze-dried to prepare sponge.

2) Preparation of fibroin matrix

Refined silk was dissolved in 8M lithium bromide aqueous solution, and the solution was put into a cellophane tube to be presented for dialysis in water. After confirming complete removal of lithium bromide, the obtained fibroin aqueous solution was poured into a polystyrene container, and was frozen for 24 hours at −10° C. Thereafter, thawing at room temperature, the nonwoven state was confirmed, and it was freeze-dried.

3) Preparation of wound covering

The mixed solution of collagen/denatured collagen obtained in 1) was poured into a stainless steel vat, and the sponge of the matrix of fibroin prepared in 2) was put on slowly, and in this state the material was quickly frozen at −30° C. and after sufficiently freezing it was freeze-dried, and a sponge of two-layer structure was obtained. Next, on a teflon substrate, a hexane solution of 50% Silastic silicone adhesive type A (Dow Corning) was applied by using a precise applicator, and a film was formed. Just after application, the sponge was put on the film so that the fibroin matrix contact to the silicone side, and after letting stand at room temperature for about 10 minutes, it was hardened in an oven for at least one hour at 60° C. Furthermore, keeping in a vacuum for an hour, the temperature was raised to 110° C., and the vacuum was maintained for 2 hours, then the temperature was lowered to room temperature, and the specimen was taken out, and the wound covering was obtained.

Example 6

In step 3) of Example 5, 25 mg of silver sulfadiazine was added to 50 cc of the mixed solution of collagen and denatured collagen, and the mixture was stirred sufficiently, and poured into a stainless steel vat. Slowly putting a matrix of fibroin, the material was quickly frozen sufficiently at −30° C., and freeze-dried, and a two-layer sponge containing antibacterial agent was obtained. By similarly laminating a silicone film on this sponge, a wound covering with antibacterial agent was obtained.

Example 7

1) Preparation of fibrous atelocollagen 1.0 g of atelocollagen was dissolved in diluted hydrochloric acid at pH3.0 to 0.3 w/v %. This solution was put in a 4° C. thermostatic oven and stirred, and phosphate buffer was added to prepare collagen solution with the final concentration of 0.1 w/v % atelocollagen, 30 mM phosphate-2-sodium, 100 mM sodium chloride. Immersing in 37° C. thermostatic bath for a day, fibrous atelocollagen (FC) solution was prepared. This solution was quickly frozen at −30° C., and freeze-dried to obtain sponge.

2) Preparation of denatured ateloocollagen solution 1.0 g of atelocollagen was dissolved in diluted hydrochloric acid at pH3.0. This solution was treated for 30 minutes in 60° C. thermostatic oven, and was left stand at room temperature for 2 hours to obtain denatured atelocollagen (HAC). The helix content of thus obtained denatured atelocollagen was about 40%.

3) Preparation of fibrous atelocollagen/denatured atelocollagen matrix

The above prepared 0.3 w/v % fibrous atelocollagen (FC) and 1 w/v % denatured atelocollagen (HAC) were mixed at 37° C., and stirred for an hour. This solution was quickly frozen at −30° C., and freeze-dried to prepare sponge.

4) Thermal dehydration crosslinking of fibrous atelocollagen

The product of 1) was evacuated for an hour in a vacuum of less than 0.05 Torr, and the temperature was lowered to 110° C., and the vacuum was maintained for 2 hours. Then, the temperature was lowered to room temperature, and the specimen was taken out.

5) Isocyanate crosslinking of fibrous atelocollagen matrix

The product of 1) was crosslinked by immersing in ethanol solution of 0.01% hexamethylene diisocyanate (HDI) for 24 hours at room temperature. It was washed in water several times to get rid of the uncrosslinked isocyanate, and freeze-dried.

6) Thermal dehydration crosslinking of fibrous atelocollagen/denatured atelocollagen matrix The product of 3) was evacuated for an hour in a vacuum of less than 0.05 Torr, and the temperature was lowered to 110° C. and the vacuum was maintained for 2 hours or 24 hours. Then, the temperature was lowered to room temperature, and the specimen was taken out.

7) In vivo subcutaneous embedding test of collagen matrices (Test 6)

The matrices obtained herein were embedded beneath the rat skin, and the tissue images were studied pathologically. For subcutaneous transplantation, female Wistar KY rats weighing about 200 g were used. Before embedding, the rats were anesthetized with Nembutal diluted five times, and the dorsal hair moistened with surgical Isodine (Meiji Seika) was carefully clipped completely by a clipping razor The clipped dorsal surface was disinfected with Isodine and ethanol.

From each cut, the incision is widened so as to form a free gap in the areola tissues beneath the dermal muscle of rat. The specimen was inserted into the gap, and was laid down flatly. The wound is sutured by nylon thread with corner needle. The wound was stitched with three sutures. The same specimen was embedded similarly in other rat.

On the 3rd day and the 28th day after embedding, the animals were killed by using ether or Nembutal diluted twice. The dermal tissues on the dorsal muscle of rat was cut out in a size of 8 cm by 12 cm or larger, keeping the embedded specimen in tissues. The tissue was put in 10% neutral buffer formalin solution, and left stand overight to be fixed, and was presented for histopathological examination.

Histopathological search was started by cutting out the specimen from the tissues. In order that the specimen be securely contained, the tissues were cut in a strip of about 0.5 cm by 2.5 cm. It was penetrated through ethanol and then xylene, and was finally replaced by paraffin. After replacing, the tissues containing the specimen were put in a hot molten liquid of solid paraffin, and cooled quickly to finish paraffin embedding. The paraffin embedded tissues were sliced by means of rotary microtome of Yamato, and 4 μm thick paraffin segments were obtained. After removing paraffin, the specimen was stained histopathologically in an arbitrary staining method to complete the preparation. As the histopatological staining, hematoxylin-eosin (HE) staining, azane staining, resorsin-fuchsin staining, and other methods may be employed. The results are shown in Table 5.

atelocollagen/denatured atelocollagen was poured into a stainless steel vat, and the sponge of fibrous atelocollagen matrix crosslinked with 0.0.% HDI prepared in 5) was slowly put on, thereby floating the sponge in the upper layer of the solution. In this state, the solution was quickly frozen at −30° C., and frozen sufficiently, and was freeze-dried in a vacuum of less than −40° C./0.1 Torr, thereby obtaining a sponge of two-layer structure composed of a fibrous atelocollagen matrix and a matrix of fibrous atelocollagen/denatured atelocollagen. Next, on a teflon substrate, hexane solution of 50% Silastic silicone adhesive type A (Dow Corning) was applied by using a precise applicator, and a film was formed. Just after application, the sponge was put on so that the fibrous atelocollagen contact to the silicone film, and after letting stand at room temperature for about 10 minutes, it was hardened in an oven for at least an hour at 60° C. In a vacuum of less than 0.05 Torr, it was evacuated for an hour, and the temperature was raised to 110° C., and the vacuum was maintained for 2 hours. Then, the temperature was lowered to room temperature, and the specimen was taken out to obtain prosthetic skin.

9) Transplantation test of artificial skin on rat skin defect wound (Test 7)

The matrix obtained above was transplanted on the dorsal skin of rat. The dorsal hair of Wistar KY rats (200 to 400 g) was clipped under Nembutal anesthesia. After disinfecting the skin with Isodine, a total skin defect wound of 20 by 20 mm was prepared by exposing the dermal muscle on the rat dorsal. Then, after hemostatic

TABLE 5

Histopatological changes in subcutaneous embedding test

| | | Tissue changes | | |
| | | Day 3 | | Day 28 |
| Specimen | Crosslinking method | Neutrophil infiltration | Fibroblast invasion | Granulation tissue atrophy |
| --- | --- | --- | --- | --- |
| FC | 0.01% HDI (Room temperature 24 H) | − | − | − |
| FC | Thermal dehydrating crosslinking (110° C., 2 H) | +++ | ++ | +++ |
| FC-10 wt. % HAC | Thermal dehydrating crosslinking (110° C., 2 H) | + | +++ | + |
| FC-20 wt. % HAC | Thermal dehydrating crosslinking (110° C., 2 H) | ++ | +++ | + |
| FC-50 wt. % HAC | Thermal dehydrating crosslinking (110° C., 2 H) | +++ | ++ | + |
| FC-10 wt. % HAC | Thermal dehydrating crosslinking (110° C., 24 H) | +++ | + | +++ |

−: negative, +: slight, ++: moderate, +++: severe HAC treated for 30 minutes at 60° C.

With FC alone, on the 3rd day, the neutrophil infiltration was intense, and fibroblast invasion was moderate, and on the 28th day, the formed granulation tissues were atrophied. By contrast, when HAC was contained by 10 or 20 wt. %, on the 3rd day, the neutrophil infiltration was weak, while the fibroblast invasion was more smooth. On the 28th day, the atrophy of granulation tissues was notably lessened.

8) Preparation of prosthetic skin

In 3), the concentration of fibrous atelocollagen was adjusted to 1.0 w/v %, and the mixed solution of fibrous process and drying, the specimen containing physiological saline was adhered. The periphery of silicone film was ligated and fixed at 16 positions by suture. Four pieces of Solfren (Termo) were laid over, and elastic tape such as Elasticon was wound around to fix oppressively. The wound site was observed 1, 2, 3, 4 weeks later, and the animals were killed for autopsy at the day 4 weeks after transplantation. Results of histopathological examinations are shown in Table 6.

TABLE 6

Gross and pathological findings in transplantation test

| Specimen | | | | Tissue changes 4 weeks later | |
|---|---|---|---|---|---|
| Upper layer matrix | Lower layer materix | HAC degeneration condition | Wound contraction | Granulation tissue | Cuticle formation |
| FC (0.01% HDI crosslinking) | FC-10 wt. % HAC (thermal dehydration crosslinking 2 hrs) | 60° C., 30 min | Weak | Granulation resembling falce corium *1 | Present |
| FC (0.01% HDI crosslinking) | FC-10 wt. % HAC (thermal dehydration crosslinking 2 hrs) | 100° C., 24 H | Weak | Granulation resembling falce corium | Present |
| FC (0.01% HDI crosslinking) | — | — | Weak | Inflammatory granulation *2 | None |
| FC-10 wt. % HAC (thermal dehydrating crosslinking) | — | 60° C., 30 min | Intense | Simple granulation *3 | Present |
| No treatment | — | — | Very intense | Simple granulation | Present |

*1: Composed of curved thick collagen fiber flux, having the gaps diffusely scattered therein with capillary vessels and fibro blasts.
*2: Compound of residual collagen fibers, giant cells, histocytes and fibroblasts phagocytizing them, and slight collagen produced by them.
*3: Granulation tissues mainly composed of fibroblasts, and sparse collagen fibers of simple structure produced by them.

EXAMPLE 8

1) Preparation of collagen sponge containing antibacterial agent

Phosphate buffer was added to 0.3% atelocollagen solution at pH3.0, and the mixture was put in a 37° C. thermostatic oven for 4 hours to prepare fibrous atelocollagen. While stirring 50 cc of fibrous atelocollagen, 25 mg, 50 mg, 250 mg, and 500 mg of powder of silver sulfadiazine were added, and dispersed sufficiently. The mixture was poured into styrol vat (10 cm × 10 cm), and freeze-dried. The prepared sponge was crosslinked for 2 hours at 110° C. in a vacuum.

2) Preparation of collagen sponge containing antibacterial agent

Phosphate buffer was added to 0.3% atelocollagen solution at pH3.0, and the mixture was put in a 37° C. thermostatic oven for 4 hours to prepare fibrous atelocollagen. This solution was freeze-dried to form sponge, and further it was crosslinked by immersing for a day in an ethanol solution of 0.01 hexamethylene isocyanate. The crosslinked collagen sponge (10 cm × 10 cm) was dipped in 100 ml of ammonia solution of silver nitrate ($1 \times 10^{-3}$ mol/liter).

3) Preparation of collagen sponge containing antibacterial agent

The collagen sponge immersed in ammonia solution of silver nitrate obtained in Example 2 was further immersed in 100 ml of sodium sulfadiazine solution ($1 \times 10^{-3}$ mol/liter).

4) Evaluation of antibacterial activity (Test 8)

Muller-Hinton agar (Difco) was treated in autoclave and maintained at 50° C., and 20 ml thereof was dispensed in Petri dish, and was left stand at room temperature for an hour to be solidified. The various bacteria cultivated on a flat disc were suspended in tris buffer solution to prepare bacterial solutions, which were applied on the entire surface of the each culture medium three times by using a swab. Specimens prepared in the previous steps were cut out in a size of 8 mm in diameter, and put on the culture medium coated with bacteria, and cultivated for 18 hours at 37° C. The results are shown in Table 7.

All strains formed nearly equal inhibition circles, not depending on the concentration of the AgSD, when addition amount is 0.25 mg/cm² or more.

TABLE 7

Antibacterial activity of collagen sponge containing antibacterial agent

| | Speciment Unit: mm | | | | | | |
|---|---|---|---|---|---|---|---|
| Species | AgSD 0 mg/cm² | AgSD 0.25 mg/cm² | AgSD 0.5 mg/cm² | AgSD 2.5 mg/cm² | AgSD 5.0 mg/cm² | Ag(NH₃)₂ | Ag(NH₃)₂— NaSD |
| Ps. aeruginosa | 0 | 11.64 | 11.64 | 10.43 | 11.64 | 9.54 | 10.68 |
| | 0 | 11.52 | 10.85 | 10.50 | 12.32 | | |
| St. epidermidis | 0 | 12.59 | 14.04 | 12.96 | 13.17 | 9.67 | 9.51 |
| | 0 | 12.93 | 12.39 | 12.67 | 13.22 | | |
| E. coli | 0 | 11.38 | 12.17 | 11.74 | 10.80 | 9.52 | 10.32 |
| | 0 | 12.78 | 12.96 | 11.58 | 11.65 | | |
| C. albicans | 0 | 17.13 | 17.23 | 15.57 | 17.15 | 8.34 | 9.31 |
| | 0 | 17.81 | 15.58 | 15.55 | 16.03 | | |

5) Preparation of artificial skin containing antibacterial agent

In Example 1, the fibrous atelocollagen solution was adjusted to 1.0 w/v %, and denatured atelocollagen solution was added. Then, 25 mg of silver sulfadiazine was added while stirring sufficiently, and the mixture was poured into a styrol vat. The fibrous atelocollagen crosslinked with 0.01% HDI was put on slowly, and freeze-dried. Next, on a teflon substrate, hexane solution of 50% Silastic silicone adhesive type A (Dow Corning) was applied by using a precise applicator, and a film was formed. Just after application, the sponge was put on, and was hardened in an oven for at least an hour at 60° C. Furthermore, evacuating for an hour in a vacuum, and the temperature was further raised to 110° C., and the vacuum was maintained for 2 hours. Then, the temperature was lowered to room temperature, and the specimen was takeout to obtain a artificial skin containing antibacterial agent.

What is claimed is:

1. A cell-penetrable medical material, comprising denatured collagen having a triple chain helix content of 0 to 80%, and a carrier possessing higher resistance to enzymatic decomposition than the denatured collagen.

2. The medical material of claim 1, wherein the denatured collagen lacks an antigenic portion at a molecular terminus.

3. The medical material of claim 1, wherein the carrier is selected from a group consisting of collagen, fibroin, polyactic acid, mucopolysaccharide, and arginic acid.

4. The medical material of claim 3, wherein the carrier is undenatured collagen.

5. The medical material of claim 3, wherein the carrier is collagen lacking an antigenic portion at a molecular terminus.

6. The medical material of claim 3, wherein the carrier is collagen with a crosslinked structure.

7. The medical material of claim 3, wherein the carrier is fibrous collagen.

8. The medical material of claim 7, wherein the fibrous collagen has a crosslinked structure.

9. The medical material of claim 1, wherein the material is a film.

10. The medical material of claim 1, wherein the carrier is dispersed in the denatured collagen.

11. The medical material of claim 1, wherein the material is a sponge.

12. The medical material of claim 11, wherein the carrier forms a spongy matrix, and the denatured collagen is contained in the spongy matrix.

13. The medical material of claim 1, wherein the ratio of denatured collagen to carrier is in the range of 5 to 80% w/v.

* * * * *

UNITED STATES PATENT AND TRADEMARK OFFICE
CERTIFICATE OF CORRECTION

PATENT NO. : 5,263,983
DATED : November 23, 1993
INVENTOR(S) : Katsutoshi YOSHIZATO et al It is certified that error appears in the above-indentified patent and that said Letters Patent is hereby corrected as shown below:

In Column 3, line 19, delete "ca" and insert -- can --.

In Column 11, line 15, delete "malin" and insert -- formalin --.

In Column 11, line 22, delete "from" and insert -- form --.

In Column 12, line 15, delete "from" and insert -- form --.

In Column 15, line 11, delete "thermostatio" and insert -- thermostatic --.

In Column 16, line 17, delete "atelooollagen" and insert -- atelocollagen --.

In Column 19, line 21, delete "histocytes" and insert -- histiocytes --.

In Column 20, line 45, delete "Speciment" and insert -- Specimen --.

In Column 21, line 23, delete "polyactic" and insert -- polylactic --.

Signed and Sealed this

Twenty-first Day of June, 1994

Attest:

BRUCE LEHMAN

*Attesting Officer*           *Commissioner of Patents and Trademarks*